(12) United States Patent  
Nitsche et al.

(10) Patent No.: US 11,598,481 B2  
(45) Date of Patent: Mar. 7, 2023

(54) DETERMINING TIMING FOR LUBRICATING FLUID CHANGE

(71) Applicant: HALLIBURTON ENERGY SERVICES, INC., Houston, TX (US)

(72) Inventors: Wolfgang Hartmut Nitsche, Humble, TX (US); John Laureto Maida, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 1071 days.

(21) Appl. No.: 16/322,778

(22) PCT Filed: Sep. 20, 2016

(86) PCT No.: PCT/US2016/052637  
§ 371 (c)(1),  
(2) Date: Feb. 1, 2019

(87) PCT Pub. No.: WO2018/056950  
PCT Pub. Date: Mar. 29, 2018

(65) Prior Publication Data

US 2021/0381641 A1 Dec. 9, 2021

(51) Int. Cl.
*F16N 29/04* (2006.01)
*G01J 3/10* (2006.01)
*G01N 33/30* (2006.01)

(52) U.S. Cl.
CPC ............... *F16N 29/04* (2013.01); *G01J 3/10* (2013.01); *G01N 33/30* (2013.01); *F16N 2200/04* (2013.01); *F16N 2260/18* (2013.01)

(58) Field of Classification Search
CPC .. F16N 29/04; F16N 2200/04; F16N 2260/18; G01J 3/10
See application file for complete search history.

(56) References Cited

U.S. PATENT DOCUMENTS

| | | | |
|---|---|---|---|
| 4,306,525 A * | 12/1981 | Faxvog | F01M 11/12 123/196 S |
| 4,742,476 A | 5/1988 | Schwartz et al. | |
| 5,194,910 A * | 3/1993 | Kirkpatrick, Jr. | G01N 21/3151 356/70 |
| 5,377,531 A | 1/1995 | Gomm | |
| 6,452,179 B1 * | 9/2002 | Coates | G01N 33/2847 250/339.09 |
| 6,839,620 B1 * | 1/2005 | Koehler | G01N 33/2888 701/108 |
| 9,176,041 B2 * | 11/2015 | Barraclough | G01N 33/2888 |

(Continued)

*Primary Examiner* — Long T Tran  
(74) *Attorney, Agent, or Firm* — Kilpatrick Townsend & Stockton LLP

(57) ABSTRACT

A method for determining when to change a lubricating fluid flowing within an apparatus includes monitoring the lubricating fluid flowing within the apparatus by passing radiation through the lubricating fluid from a radiation source. The lubricating fluid is analyzed for a presence of particles in the lubricating fluid based on the radiation passing through the lubricating fluid. A concentration of the particles in the lubricating fluid is determined when the presence of particles is detected. An alert to change the lubricating fluid is generated when the concentration of particles in the lubricating fluid exceeds a threshold.

20 Claims, 4 Drawing Sheets

(56) References Cited

U.S. PATENT DOCUMENTS

| | | | | |
|---|---|---|---|---|
| 2004/0213373 A1* | 10/2004 | Wilson | ............... | G01N 33/2858 |
| | | | | 378/42 |
| 2005/0057267 A1* | 3/2005 | Nicholson | .......... | G01N 33/2888 |
| | | | | 324/698 |
| 2008/0207474 A1* | 8/2008 | Damm | ................. | G01M 3/202 |
| | | | | 73/40 |
| 2010/0036619 A1* | 2/2010 | Bolt | ................... | G01N 33/2888 |
| | | | | 702/50 |
| 2011/0059876 A1* | 3/2011 | Takahama | ............ | C10M 173/02 |
| | | | | 977/773 |
| 2011/0166051 A1* | 7/2011 | Mizrahi | ............... | C10M 161/00 |
| | | | | 428/407 |
| 2016/0069852 A1* | 3/2016 | Lefeber | ................. | G01N 21/94 |
| | | | | 250/227.23 |

* cited by examiner

DETERMINING TIMING FOR LUBRICATING FLUID CHANGE

FIELD

The present disclosure relates to evaluating the condition of lubricating fluids and, more particularly, to analyzing lubricating fluids to determine if the lubricating fluid needs to be changed or replaced.

BACKGROUND

Many machines and tools are internally lubricated by lubricating fluids, such as lubricating oil, which has to be replaced periodically. The life expectancies of engines are influenced by the quality of the lubricating oil, which serves to protect engine parts against wear during operation. The most widely known example is car engine oil, which typically requires an oil change at least once per year. Similarly, periodic oil changes are performed in various machines used in the oil field industry. As the quality of engine oil degrades over time, the engine oil's ability to protect the engine against wear degrades, and eventually has to be replaced to prevent the machine from being damaged. Typically, oil changes are simply performed at fixed intervals, for example once per year, or after every five hundred hours of using the machine.

Such conventional methods and systems have generally been considered satisfactory for their intended purpose. However, there is still a need in the art for timely determination and/or detection of need for lubricating fluid change. The present disclosure provides a solution for this need.

BRIEF DESCRIPTION OF THE DRAWINGS

So that those skilled in the art to which the subject disclosure appertains will readily understand how to make and use the devices and methods of the subject disclosure without undue experimentation, embodiments thereof will be described in detail herein below with reference to certain figures, wherein.

DETAILED DESCRIPTION

The following discussion is presented to enable a person skilled in the art to make and use the exemplary disclosed embodiments. Various modifications will be readily apparent to those skilled in the art, and the general principles described herein may be applied to embodiments and applications other than those detailed below without departing from the spirit and scope of the disclosed embodiments as defined herein. Accordingly, the disclosed embodiments are not intended to be limited to the particular embodiments shown, but are to be accorded the widest scope consistent with the principles and features disclosed herein. For example, while various embodiments described herein relate to use of lubricating oil, other embodiments may use other suitable lubricating fluids.

The ability of lubricating oil to protect the engine against wear is directly related to the quality of the lubricating oil. However, the rate of degradation of lubricating oil may vary depending on numerous factors and changing the oil at fixed time intervals may not be appropriate. Consequently, it is important to decide the right time interval between oil changes. If oil changes are performed more often than required, this can cause unnecessary expenses and possible down-time. On the other hand, waiting too long before performing an oil change could damage the machine or degrade its performance.

Moreover, if the oil is degraded, more wear of the machine may occur, which may result in metal particles (e.g., metal flakes) being worn off of various engine components. These metal particles may afterwards be carried away by the engine oil. This means that as long as the oil fulfills its purpose and reduces wear of the machine's components, the concentration of metal particles in the oil should be close to zero. However, as soon as degradation of the engine oil reaches a point that wear of the machine's components takes place, metal particles will appear within the engine oil. As such, the best time to perform an oil change is as soon as metal particles start to appear within the oil.

Embodiments herein use a spectroscopy setup (e.g., terahertz (THz) spectroscopy setup) which measures the presence or absence of particles, such as metal particles, in the lubricating oil in real-time or near real-time. Embodiments herein can generate an indication/alert that an oil change is required as soon as metal particles appear and/or the amount of metal particles in the lubricating oil exceeds a certain threshold. Accordingly, the lubricating oil can be replaced at the right time.

Figure 1:
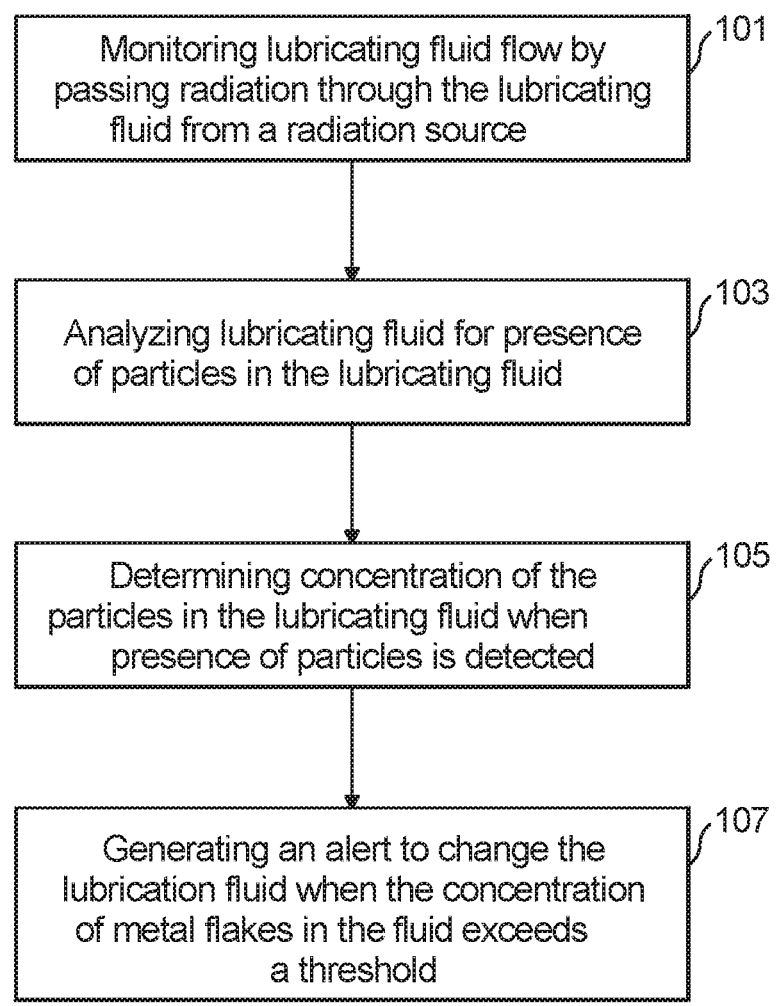
FIG. 1 is a schematic view of an exemplary embodiment of a method for determining timing for a lubricating fluid change.

Referring to the figures, FIG. 1 shows an exemplary method 100 for determining timing for a lubricating oil change, according to an embodiment described herein. At step 101, lubricating oil flow is monitored by passing radiation through the lubricating fluid from a radiation source. Types of radiation that may be used include electromagnetic radiation such as THz electromagnetic radiation, infrared light, visible light, microwaves, x-rays and y-rays, and other types of radiation such as α-rays and β-rays. An exemplary radiation source may be a THz radiation source. The radiation source may also be a light source, for example a source of visible light. At step 103, the lubricating fluid is analyzed for presence of particles in the lubricating fluid flow. Particles may include metal particles, additives, water, soot, coke, etc. Particles may also be materials such as silicone or rubber/plastic particles from bushings and seals. In addition, embodiments herein can use spectroscopy to check the length of the oil molecules and detect the molecular breakdown of long chained hydrocarbons. Analysis may be performed using a spectrometer, for example, a THz domain spectrometer. At step 105, concentration of the particles in the lubricating fluid flow may be determined and/or calculated when presence of particles is detected. At step 107, an alert to change the lubricating fluid may be generated when the concentration of particles, e.g., metal particles, in the oil flow exceeds a threshold. For example, the threshold of metal particles may be based on an increase over a given time window such as a certain rate over time (e.g., if the rate of increase exceeds ten metal particles per cubic centimeter of oil per hour). As another example, the threshold may be based on attenuation increases by a certain level within a period of time.

In certain embodiments, the indication/alert to change the oil and/or quality of the lubricating oil may be shown on a display unit, for example, as an oil quality gauge on a visual interface (e.g., a screen on a computer device, vehicle dashboard, etc.). Embodiments herein may be useful for oil field diesel power generators, gear boxes, hydraulic oil in electric pumps, hydraulic oil in general, as well as for engine lubrication oil.

Figure 2:
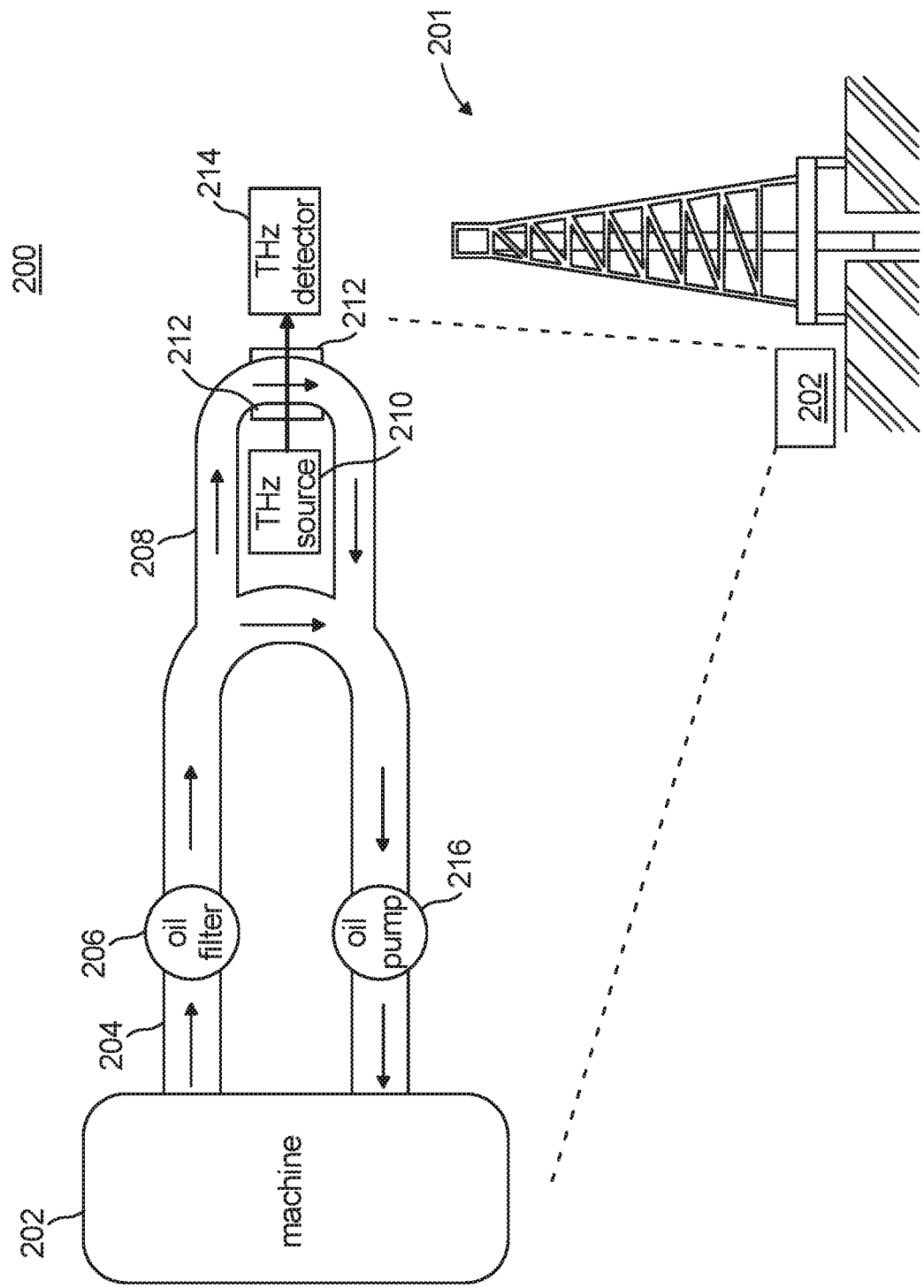
FIG. 2 is a schematic view of an exemplary embodiment of a system implementing the method of FIG. 1.

FIG. 2 shows an exemplary embodiment of a system 200 implementing the method 100 described in FIG. 1 above, for example, for an oil drilling rig 201. System 200 may be or may include a machine or apparatus 202, such as a pump or a generator for the drilling rig 201, having an engine or motor that uses a lubricating fluid, for example, motor oil. Machine 202 may include a pipe 204 through which motor oil flows, (as indicated by the arrows) an oil filter 206 operatively connected to and placed in the path of the pipe 204, and an oil pump 216. The oil filter 206 may be configured to filter debris and particles in the motor oil, and the oil pump 216 may be configured to circulate the motor oil through various components in system 200.

System 200 may also include a bypass line 208 that splits off from pipe 204 so as to direct a portion of the motor oil through the bypass line 208. The bypass line 208 may circulate through a region configured with a spectrometer, such as a THz spectrometer, composed of a THz source 210 and a THz detector 214. Monitoring the motor oil could be realized by allowing the motor oil to flow through bypass line 208 (e.g., a thin plastic transparent pipe) having two small windows 212 on opposite sides of the bypass line 208 and sending THz radiation from THz source 210 through the oil via one of the windows 212. Then, the THz radiation may be detected after it radially travels through the bypass line 208 and the oil and passes through the other one of windows 212. THz detector 214 may measure the power and/or the spectral composition of the THz radiation after the THz radiation travels through the oil. From this spectroscopic data, the concentration of metal particles in the oil can be determined, since metal particles will be much more radiation-absorbent than pure oil. At least a portion of the spectrometer may be implemented as software and/or hardware having a processor coupled to a memory, the memory configured to store computer readable instructions that may be executed by the processor to implement one or more steps of method 100.

The THz spectrometer essentially determines the concentration of metal particles within the lubricating oil/fluid. For example, certain THz frequencies may be absorbed by metal particles but not by the oil. If most of the radiation passes through, then it is unlikely that an oil change is needed. However, as soon as the measurement drops, then metal particles are likely present in the oil. If the engine is running and the spectroscopy system is running continuously or at regular intervals (e.g., sampling every minute or every hour), appearance of metal particles can be constantly monitored in real-time or near real-time. As soon as the concentration of metal particles surpasses some pre-defined threshold, the spectrometer could, for example, activate a warning light which reminds the user that it is time for an oil/fluid change. The spectrometer could be calibrated beforehand. Calibration may be performed by first filling the pipe with "reference oil" which contains a threshold or critical concentration of metal particles at which an oil change is needed or desired. Then, radiation is passed through the reference oil and a measurement taken to determine how much of the radiation passed through the reference oil. Subsequently, while the engine is in use, as soon as the radiation transmission level drops to approximately the same threshold level as was observed during the calibration, it may be assumed the time is right for an oil change.

The threshold may be manually set by a user or pre-set by a program or a manufacturer. Moreover, when metal particles are present, the reflectivity of the metal particles may also increase the reflectivity of the oil in the reflective mode of operation of the THz spectrometer, or it may increase the radiation loss in the transmissive mode. Typically, the THz radiation would travel through the oil regardless of the color of the oil because the wavelength of THz radiation is relatively long (in the range of 3 mm-30 μm). However, metal particles in an otherwise normal volume of oil would reflect the THz radiation (or other electromagnetic radiation). As such, it would cause a transmissive attenuation or an increase in reflectivity in the reflective mode of operation. As shown in FIG. 2, the oil first passes through an oil filter 206, which could potentially remove some of the larger metal particles. Therefore, in certain embodiments, the bypass line 208 can be positioned before the oil filter 206 to detect even those metal particles which are too large to pass through the oil filter 206.

In certain embodiments, in addition to checking for the presence of metal particles, the system 200 could use spectroscopy to determine the quality of the oil by confirming the presence of certain desired molecules (e.g., additives) as well as the absence of undesired molecules and particles (e.g., water, soot, coke). Examples of desirable additives include but are not limited to detergents, surfactants, anti-foaming agent, wetting agents, and polymer swelling agents. In some embodiments, the THz spectrometer may also be set up to detect acids, bases, varnishes, other organic and inorganic compounds of interest in the oil.

Figure 3:
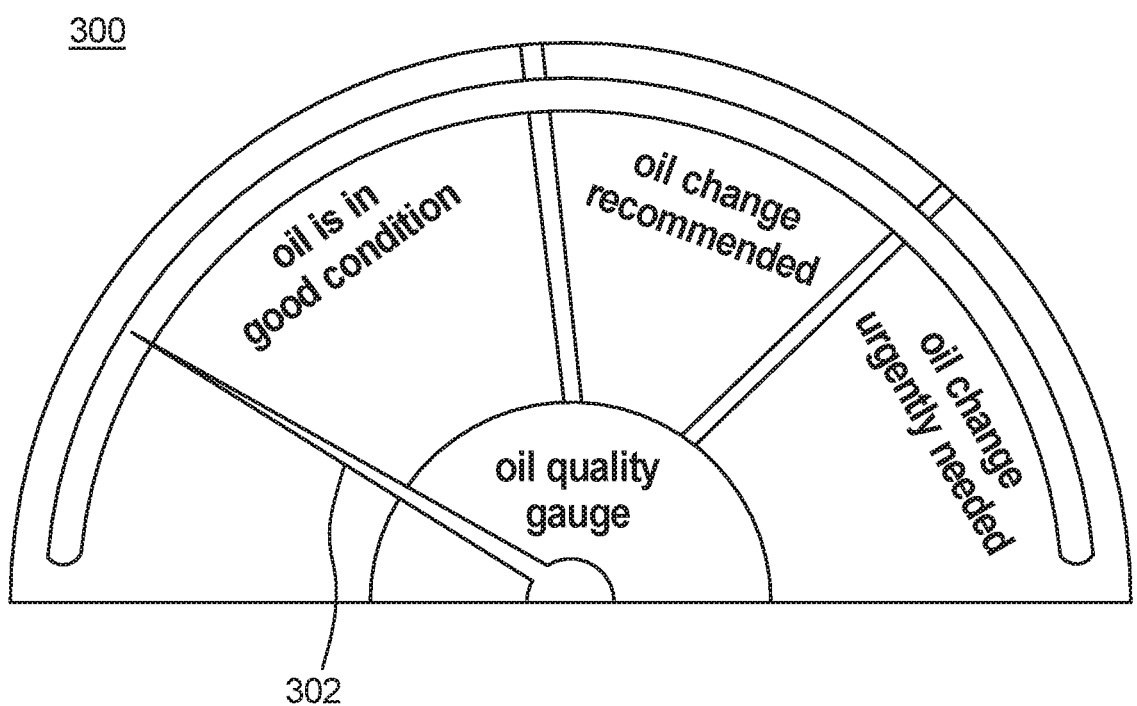
FIG. 3 is a schematic view of an exemplary gauge for showing results of a system implementing the method of claim 1.

FIG. 3 shows an exemplary gauge 300 for displaying the results of system 200 implementing method 100. As shown, gauge 300 displays the result of the spectroscopy (e.g., THz spectroscopy) on an easy to understand oil quality gauge. The results may be related to the current concentration of metal particles in the oil such that if the concentration of metal particles is low, a needle/pointer 302 of gauge 300 may point to a region indicating that the oil is in good condition (e.g., in a green range); if the concentration of metal particles is sufficiently high to warrant an oil change, the needle/pointer 302 may point to a region indicating that an oil change is recommended (e.g., a yellow range); and if the concentration of metal particles is so high that continuing the use of the motor might result in permanent engine damage, the needle/point 302 moves to a region indicating that oil change is urgently needed (e.g., a red range). Gauge 300 may be configured for display on a monitor of a device or dashboard or any suitable device having a visual display unit.

Figure 4:
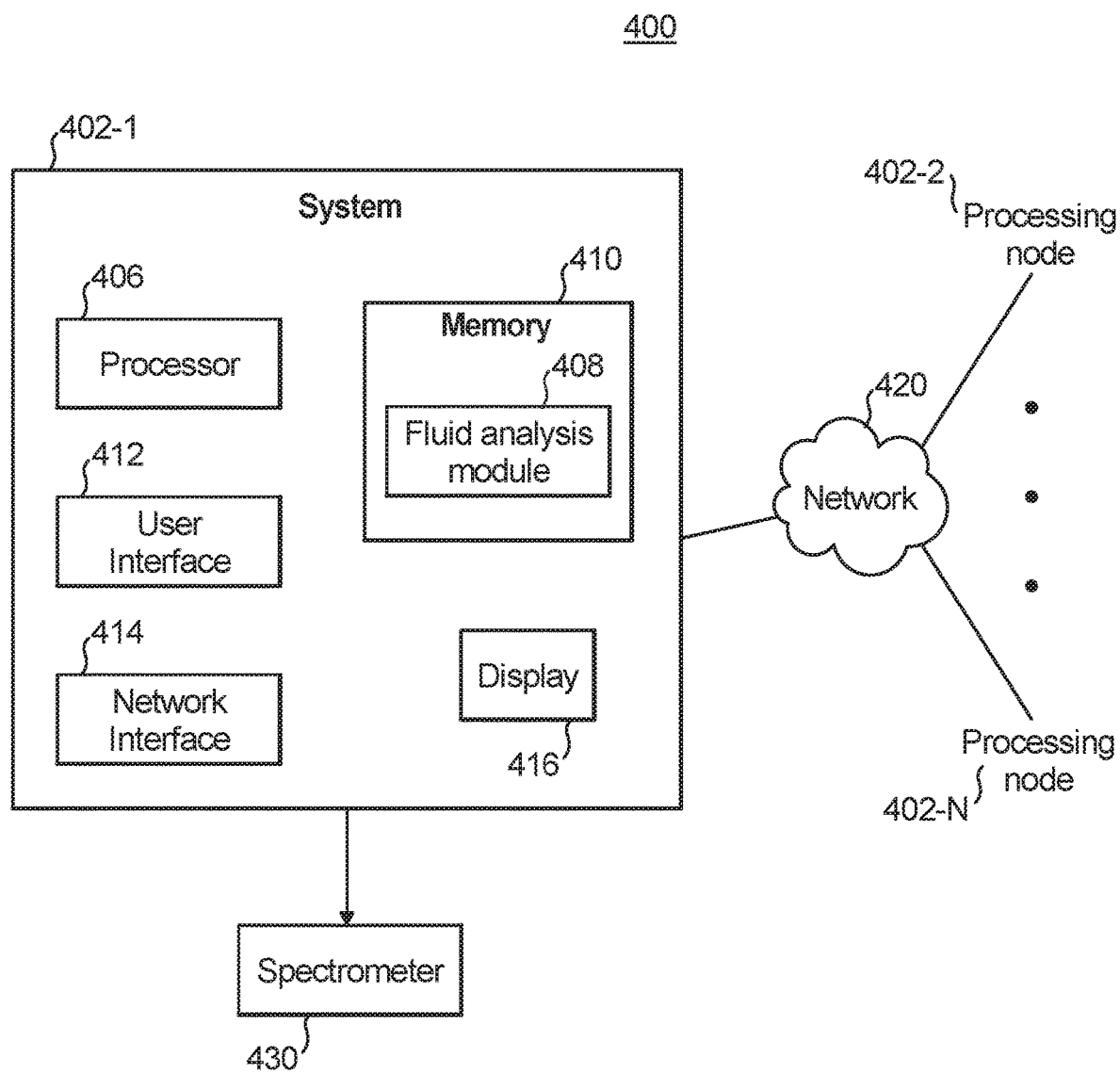
FIG. 4 is a schematic view of an exemplary embodiment of a network in which the methodology of FIG. 1 may be implemented.

FIG. 4 shows an exemplary distributed network 400 for implementing method 100 of FIG. 1. Distributed network 400 comprises one or more processing nodes 402-1 . . . 402-N configured for communication through network 420. Each of the processing nodes 402-1 . . . 402-N may be configured with components similar to computer system 402-1, which may comprise, but is not limited to, in-vehicle computer systems, personal computer systems, server computer systems, hand-held or laptop devices, multiprocessor systems, microprocessor-based systems, network PCs, and the like. Computer system 402-1 may include a user interface 412, a network interface 414, one or more processors 406 coupled to a memory 410 and a display 416. Computer system 402-1 may be operatively connected to a spectrometer 430 (e.g., a THz spectrometer as described in the context of FIG. 2) and configured to communicate with spectrometer 430 to receive and transmit data therebetween.

User interface 412 may be configured to enable user input into the computer system 402-1. Network interface 414 may be configured to enable the computer system 402-1 to interface with a network 420 and other system components in a distributed network. Memory 410 may include a random-access semiconductor memory, storage device, or storage medium (either volatile or non-volatile) for storing or encoding data and programs. In another embodiment, the memory 410 represents the entire virtual memory of the computer system 402-1, and may also include the virtual memory of other computer systems coupled to computer system 402-1 or connected via network 420. Memory 410 may also comprise a fluid analysis module 408 for implementing at least a portion of method 100 of FIG. 1. The display 416 may be a standalone display screen, on-dash monitor of a vehicle, computer monitor, a tablet or handheld device display, or other suitable displayable device. It is to be appreciated that distributed network 400 may include more or less components than shown in FIG. 4. Furthermore, each of the processing nodes 402-1 . . . 402-N may comprise more or less components than shown in computer system 402-1.

Embodiments herein provide a method for determining when to change a lubricating fluid flowing within an apparatus. The method comprises monitoring the lubricating fluid flowing within the apparatus by passing radiation through the lubricating fluid from a radiation source, analyzing the lubricating fluid for a presence of particles in the lubricating fluid based on the radiation passing through the lubricating fluid, determining a concentration of the particles in the lubricating fluid when the presence of particles is detected, and generating an alert to change the lubricating fluid when the concentration of particles in the lubricating fluid exceeds a threshold.

In aspects, the lubricating fluid may comprise oil. In aspects, the particles may comprise at least one of metal particles, additives, water, soot and coke. In aspects, the radiation may comprise one of terahertz radiation, electromagnetic radiation, α-radiation and β-radiation.

In aspects, analyzing the lubricating fluid for the presence of particles may comprise measuring the radiation that passed through the lubricating fluid using a spectrometer. In aspects, determining the concentration of particles may comprise using a data processing device to evaluate changes in reflectivity of the lubricating fluid. In aspects, determining the concentration of particles may comprise using a data processing device to evaluate changes in transmissivity of the lubricating fluid.

In aspects, the threshold may comprise one of: a rate of increase in number of particles over a period of time, and a level of increase in attenuation over the period of time. In aspects, the method may further comprise showing a quality level of the lubricating fluid on a display. In aspects, generating the alert may comprise showing a warning on the display. In aspects, monitoring may be performed according to one of continuously and periodically.

Embodiments herein also provide a computer program product for determining when to change a lubricating fluid flowing within an apparatus, the computer program product comprising a computer readable storage medium readable by a processing device and storing instructions for execution by the processing device. The instructions cause the processing device to perform a method comprising monitoring the lubricating fluid flowing within the apparatus by passing radiation through the lubricating fluid from a radiation source, analyzing the lubricating fluid for a presence of particles in the lubricating fluid based on the radiation passing through the lubricating fluid, determining a concentration of particles in the lubricating fluid when the presence of particles is detected, and generating an alert to change the lubricating fluid when the concentration of particles in the lubricating fluid exceeds a threshold.

In aspects, the instructions for analyzing the lubricating fluid for the presence of particles may comprise instructions for measuring the radiation that passed through the lubricating fluid using a spectrometer. In aspects, the instructions for determining the concentration of particles may comprise instructions for using the processing device to evaluate changes in reflectivity of the lubricating fluid. In aspects, the instructions for determining the concentration of particles may comprise instructions for using the processing device to evaluate changes in transmissivity of the lubricating fluid. In aspects, the processor may further be configured to show a quality level of the lubricating fluid on a display.

Embodiments herein also provide a system for determining when to change a lubricating fluid flowing within an apparatus. The system comprises a radiation source configured to generate radiation that passes through the lubricating fluid flowing within the apparatus, a radiation detector configured to detect radiation that passed through the lubricating fluid, and a processing device operatively coupled to a memory having instructions stored thereon. When executed by the processing device, the instructions cause the processing device to receive information from the radiation detector to monitor the lubricating fluid for a presence of particles, determine a concentration of particles in the lubricating fluid when the presence of particles is detected, and generate an alert to change the lubricating fluid when the concentration of particles in the lubricating fluid exceeds a threshold.

In aspects, the radiation source may comprise a terahertz radiation generator. In aspects, the radiation detector may comprise a terahertz spectrometer. In aspects, the system may further comprise a display operable to show a quality level of lubricating fluid in the apparatus.

While the invention has been described with reference to one or more particular embodiments, those skilled in the art will recognize that many changes may be made thereto without departing from the spirit and scope of the description. Each of these embodiments and obvious variations thereof is contemplated as falling within the spirit and scope of the claimed invention, which is set forth in the following claims.

What is claimed is:

1. A method for determining when to change a lubricating fluid flowing within an apparatus, comprising:
   monitoring the lubricating fluid flowing within the apparatus, by passing radiation through the lubricating fluid from a radiation source at a location where the lubricating fluid is flowing through a pipe that carries the lubricating fluid to or from the apparatus;
   analyzing the lubricating fluid flowing through the pipe for a presence of particles in the lubricating fluid based on the radiation passing through the lubricating fluid;
   determining a concentration of the particles in the lubricating fluid flowing through the pipe when the presence of particles is detected; and
   generating an alert to change the lubricating fluid when the concentration of particles in the lubricating fluid flowing through the pipe exceeds a threshold.

2. The method of claim 1, wherein the lubricating fluid comprises oil.

3. The method of claim 1, wherein the particles comprise at least one of metal particles, additives, water, soot and coke.

4. The method of claim 3, wherein the radiation comprises one of terahertz radiation, electromagnetic radiation, α-radiation and β-radiation.

5. The method of claim 1, wherein analyzing the lubricating fluid flowing through the pipe for the presence of particles comprises measuring the radiation that passed through the lubricating fluid flowing through the pipe using a spectrometer.

6. The method of claim 1, wherein determining the concentration of particles comprises using a data processing device to evaluate changes in reflectivity of the lubricating fluid flowing through the pipe.

7. The method of claim 6, wherein the threshold comprises one of: a rate of increase in number of particles over a period of time; and a level of increase in attenuation over the period of time.

8. The method of claim 7, further comprising showing a quality level of the lubricating fluid on a display.

9. The method of claim 8, wherein generating the alert comprises showing a warning on the display.

10. The method of claim 1, wherein determining the concentration of particles comprises using a data processing device to evaluate changes in transmissivity of the lubricating fluid flowing through the pipe.

11. The method of claim 1, wherein monitoring is performed continuously or periodically.

12. A computer program product for determining when to change a lubricating fluid flowing within an apparatus, the computer program product comprising a computer readable storage medium readable by a processing device and storing instructions for execution by the processing device for performing a method comprising:
   monitoring the lubricating fluid flowing within the apparatus, by passing radiation through the lubricating fluid from a radiation source at a location where the lubricating fluid is flowing through a pipe that carries the lubricating fluid to or from the apparatus;
   analyzing the lubricating fluid flowing through the pipe for a presence of particles in the lubricating fluid based on the radiation passing through the lubricating fluid;
   determining a concentration of particles in the lubricating fluid flowing through the pipe when the presence of particles is detected; and
   generating an alert to change the lubricating fluid when the concentration of particles in the lubricating fluid flowing through the pipe exceeds a threshold.

13. The computer program product of claim 12, wherein the instructions for analyzing the lubricating fluid for the presence of particles comprise instructions for measuring the radiation that passed through the lubricating fluid flowing through the pipe using a spectrometer.

14. The computer program product of claim 12, wherein the instructions for determining the concentration of particles comprises instructions for using the processing device to evaluate changes in reflectivity of the lubricating fluid flowing through the pipe.

15. The computer program product of claim 12, wherein the instructions for determining the concentration of particles comprises instructions for using the processing device to evaluate changes in transmissivity of the lubricating fluid flowing through the pipe.

16. The computer program product of claim 12, further comprising instructions for showing a quality level of the lubricating fluid on a display.

17. A system for determining when to change a lubricating fluid flowing within an apparatus, comprising:
   a radiation source configured to generate radiation that passes through the lubricating fluid at a location where the lubricating fluid is flowing through a pipe that carries the lubricating fluid to or from the apparatus;
   a radiation detector configured to detect radiation that passed through the lubricating fluid flowing through the pipe;
   a processing device operatively coupled to a memory having instructions stored thereon that, when executed by the processing device, causes the processing device to:
   receive information from the radiation detector to monitor the lubricating fluid flowing through the pipe for a presence of particles;
   determine a concentration of particles in the lubricating fluid flowing through the pipe when the presence of particles is detected; and
   generate an alert to change the lubricating fluid when the concentration of particles in the lubricating fluid flowing through the pipe exceeds a threshold.

18. The system of claim 17, wherein the radiation source comprises a terahertz radiation generator.

19. The system of claim 17, wherein the radiation detector comprises a terahertz spectrometer.

20. The system of claim 17, further comprising a display operable to show a quality level of the lubricating fluid flowing in the apparatus.

* * * * *